(12) United States Patent
Ichinohe

(10) Patent No.: US 8,168,735 B2
(45) Date of Patent: May 1, 2012

(54) SILICONE COMPOUND, A PROCESS FOR THE PREPARATION THEREOF AND A PROCESS FOR THE PREPARATION OF AN OPHTHALMIC DEVICE THEREFROM

(75) Inventor: Shoji Ichinohe, Takasaki (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 26 days.

(21) Appl. No.: 12/472,066

(22) Filed: May 26, 2009

(65) Prior Publication Data
US 2009/0299022 A1    Dec. 3, 2009

(30) Foreign Application Priority Data
May 27, 2008    (JP) ................................ 2008-137511

(51) Int. Cl.
*G02B 1/04*    (2006.01)
*C08F 30/08*    (2006.01)

(52) U.S. Cl. ............. 526/279; 528/25; 528/26; 528/31; 523/107; 526/310; 526/319; 526/321; 526/323; 526/323.1

(58) Field of Classification Search .................. None
See application file for complete search history.

(56) References Cited

U.S. PATENT DOCUMENTS

| | | | |
|---|---|---|---|
| 3,808,178 A | 4/1974 | Gaylord | |
| 4,602,074 A | 7/1986 | Mizutani et al. | |
| 5,985,793 A * | 11/1999 | Sandbrink et al. | 504/363 |
| 6,171,422 B1 * | 1/2001 | Cahill et al. | 156/150 |
| 6,288,129 B1 * | 9/2001 | Gruning et al. | 516/23 |
| 6,867,246 B2 * | 3/2005 | Nowak et al. | 523/109 |
| 6,867,325 B2 * | 3/2005 | Kato et al. | 556/439 |
| 2004/0171783 A1 * | 9/2004 | Cook et al. | 528/25 |
| 2004/0192873 A1 * | 9/2004 | Okuhira et al. | 528/25 |
| 2007/0238845 A1 * | 10/2007 | Hashimoto | 527/100 |
| 2009/0234089 A1 * | 9/2009 | Ueyama et al. | 526/279 |

FOREIGN PATENT DOCUMENTS

| | | |
|---|---|---|
| EP | 0 425 436 A2 | 5/1991 |
| EP | 0 940 693 A2 | 9/1999 |
| EP | 1 386 924 A1 | 2/2004 |
| JP | 52-33502 B | 8/1977 |
| JP | 59-78236 A | 5/1984 |
| JP | 61-57612 A | 3/1986 |
| JP | 3-12415 A | 1/1991 |
| JP | 2001-55446 A | 2/2001 |
| JP | 2001-098040 * | 10/2001 |
| JP | 2007-001918 | 1/2007 |
| JP | 2007-186709 A | 7/2007 |
| WO | 2008/008752 A2 | 1/2008 |

OTHER PUBLICATIONS

"Organic Chemistry" authored by Carey and published by McGraw Hill © 1987.*
Machine translation of JP 2001-055446.*
European Search Report for corresponding European Application No. 09161126.9 dated Aug. 3, 2009.

* cited by examiner

*Primary Examiner* — Marc Zimmer
(74) *Attorney, Agent, or Firm* — Birch, Stewart, Kolasch & Birch, LLP

(57) ABSTRACT

The present invention provides a hydrophilic silicone which has a predetermined number of silicon atoms and a high purity and is suitable for producing an ophthalmic device and a process for preparing the same.

The silicone compound is represented by formula (1) with a purity of 95% by weight or higher,

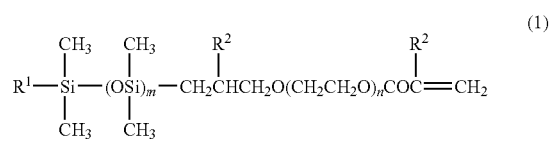

wherein m is one value out of the integers of from 3 to 10, n is one value out of the integers of from 1 to 10, $R^1$ is one out of alkyl groups having 1 to 4 carbon atoms, and $R^2$ is one out of a hydrogen atom and a methyl group.

9 Claims, 2 Drawing Sheets

SILICONE COMPOUND, A PROCESS FOR THE PREPARATION THEREOF AND A PROCESS FOR THE PREPARATION OF AN OPHTHALMIC DEVICE THEREFROM

CROSS REFERENCES

This application claims benefits of Japanese Patent Application No. 2008-137511 filed on May 27, 2008, the contents of which are hereby incorporated by reference.

FIELD OF THE INVENTION

The present invention relates to a silicone compound for producing an ophthalmic device, such as a contact lens, an intraocular lens, and an artificial cornea, hereinafter sometimes referred to as "a monomer for ophthalmic use", and to a process for preparing the same. In particular, the present invention relates to a silicone compound which has a silicone moiety having a predetermined molecular weight and is copolymerized with a monomer such as a (meth)acrylic monomer to give a polymer which is suitable for ophthalmic application and has a high transparency and a high oxygen transmission rate, as well as to a process for preparing the same.

BACKGROUND OF THE INVENTION

As monomers for ophthalmic use, the following silicone compounds are known.

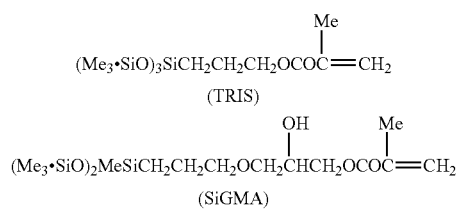

The afore-mentioned TRIS, 3-[tris(trimethylsiloxy)silyl]propyl methacrylate, has poor compatibility with hydrophilic monomers, such as, 2-hydroxyethyl methacrylate (HEMA). Therefore, when TRIS is copolymerized with hydrophilic monomers, such a drawback occurs that a transparent polymer is not obtained. Meanwhile, SIGMA described above has good compatibility with hydrophilic monomers such as HEMA. Their copolymers are characterized by a relatively high oxygen transmission rate and a hydrophilic property. However, recently, a higher oxygen transmission rate is required for a polymer for ophthalmic use so that a user can continuously wear contact lenses for a longer term. The polymers obtained from SiGMA are insufficient in terms of the oxygen transmission rate.

In order to solve this problem, the compound represented by the following formula (a), hereinafter referred to as "(a)", was proposed in the following Patent Literature 1.

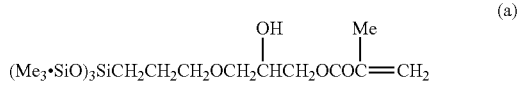

The weight ratio of the Si-containing moiety, i.e., bis(trimethylsiloxy)methylsilyl in SIGMA and tris(trimethylsiloxy)silyl in (a), to the whole molecule is 52% for SIGMA and 60% for (a). The higher weight ratio of the Si-containing moiety seems to give the higher oxygen transmission rate.

SiGMA is a trimeric silicone which has three silicon atoms and (a) is a tetrameric silicone which has four silicon atoms. It seems that tetrameric or higher one is preferred for oxygen transmission. The weight ratio of the Si moiety in TRIS, tetrameric silicone, is 70% with a purity of 98% is commercially available.

When the weight ratio of the Si moiety is increased in order to increase the oxygen transmission rate, the molecular weight per polymerizable group increases and, therefore, strength of the copolymer decreases. Tetrameric and pentameric silicones seem to be preferable in order to attain both good oxygen transmission rate and strength of the copolymer.

The afore-mentioned (a) is prepared by reacting a corresponding epoxy precursor with methacrylic acid. There is a problem that many side reactions occur, so that properties of the resulting copolymers are various.

Meanwhile, as a method for the preparation of a silicone which is vinyl-polymerizable, a method is known from Patent Literature 3 where a cyclic siloxane is anion-polymerized with a lithium trialkylsilanolate as an initiator, which is then reacted with a chlorosilane which has a (meth)acryl group, such as 3-(2-methacryloyloxy ethoxy)propyl dimethyl chlorosilane to prepare the silicone represented by the following formula (b).

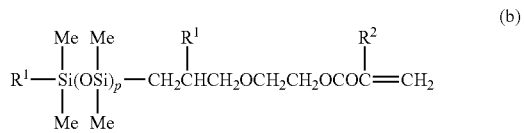

In the afore-mentioned method, a silicone chain which has a high polymerization degree of the cyclic siloxane is formed. When the silicone is mixed with a hydrophilic monomer, such as 2-hydroxyethyl methacrylate, turbidity occurs sometimes. Additionally, a ratio of the end-blocking of the silicone chain by the chlorosilane is not high.

Another method is also known from Patent Literature 4, where a silicone represented by the following formula (c) is prepared by esterifying a (meth)acrylic acid or transesterifying a (meth)acrylate with an organopolysiloxane having a hydroxyl group on its one end,

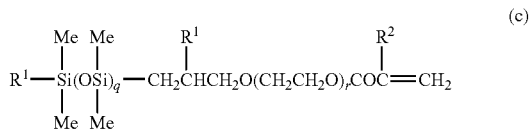

wherein r is an integer of 3 or larger.

In the above-described method, the esterification ratio is insufficient, the end blocking ratio is low, and the distribution of the degree of polymerization of the silicone is broad. Patent Literature 4 refers also to a preparation method where an unsaturated compound having a (meth)acryl group is hydrosililated with an organopolysiloxane having an SiH group on its one end. However, in this method, the hydrosililation of the (meth)acrylic moiety of the unsaturated compound having a (meth)acryl group also takes place and, therefore, the desired compound cannot be obtained in a high purity.

[Patent Literature 1] Japanese Patent Application Laid-Open No. 2007-186709
[Patent Literature 2] Japanese Patent Application Laid-Open No. 2007-1918
[Patent Literature 3] Japanese Patent Application Laid-Open No. Sho-59-78236
[Patent Literature 4] Japanese Patent Application Laid-Open No. 2001-55446

DISCLOSURE OF THE INVENTION

Problems to be Solved by the Invention

The purposes of the present invention are to provide a hydrophilic silicone which has a predetermined number of silicon atoms and is highly pure and preferred as a monomer for ophthalmic use, to provide a process for preparing the same, and to provide a process for the preparation of an ophthalmic device therefrom.

Means to Solve the Problems

The present invention is a silicone compound represented by formula (1) with a purity of 95% by weight or higher,

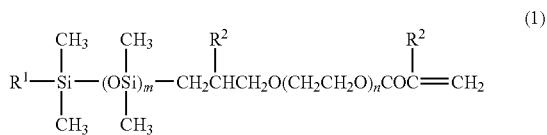

wherein m is one value out of the integers of from 3 to 10, n is one value out of the integers of from 1 to 10, $R^1$ is one out of alkyl groups having 1 to 4 carbon atoms, and $R^2$ is one out of a hydrogen atom and a methyl group.

Another aspect of the present invention is a process for preparing the silicone compound represented by the following formula (1),

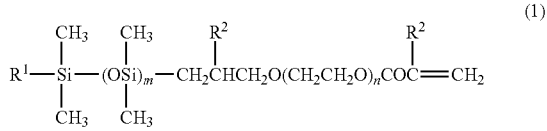

wherein m is an integer of from 3 to 10, n is an integer of from 1 to 10, $R^1$ is an alkyl group having 1 to 4 carbon atoms, and $R^2$ is a hydrogen atom or a methyl group, characterized in that the process comprises a step of reacting a silicone compound represented by the following formula (2),

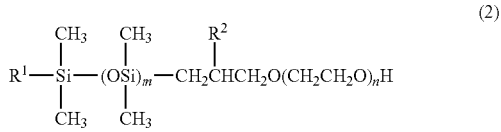

wherein m, n, $R^1$ and $R^2$ are as defined above, with a (meth)acrylic acid halide represented by the following formula (3),

wherein X is Cl, Br, or I and $R^2$ is as defined above.

Effects of the Invention

The compound of the present invention for producing an ophthalmic device has a high purity. The compound can be copolymerized with a polymerizable monomer such as a (meth)acrylic monomer to provide a polymer which is colorless and transparent even when the polymer contains water. The present process uses a reaction of a silicone compound having a hydroxyl group with an acid chloride, so that a silicone monomer is obtained which has a high end-blocking ratio and a high purity.

BEST EMBODIMENTS TO WORK THE INVENTION

Figure 1:
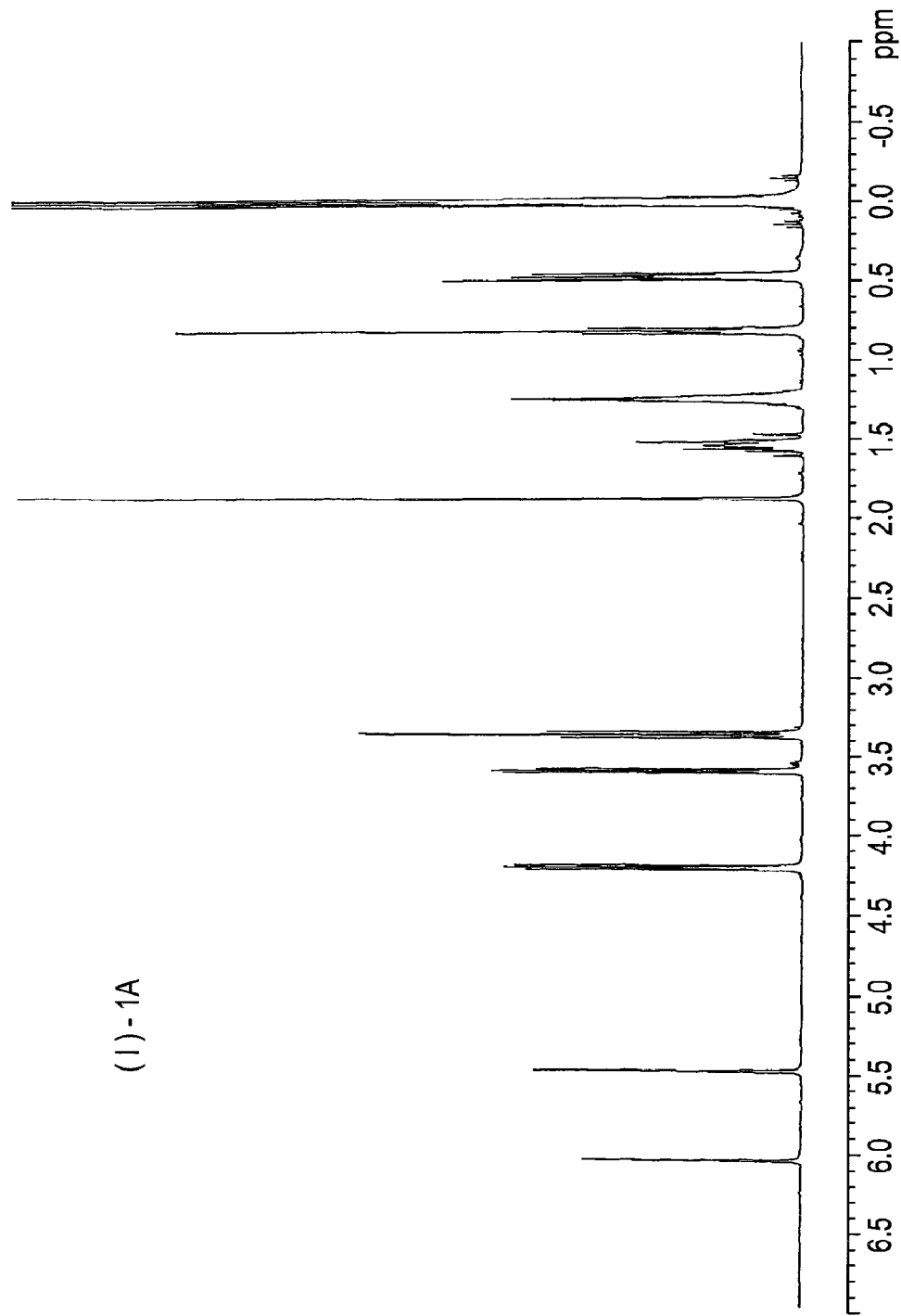
FIG. 1 shows $^1$H-NMR spectra of the silicone which was prepared in Example 1.
Figure 2:
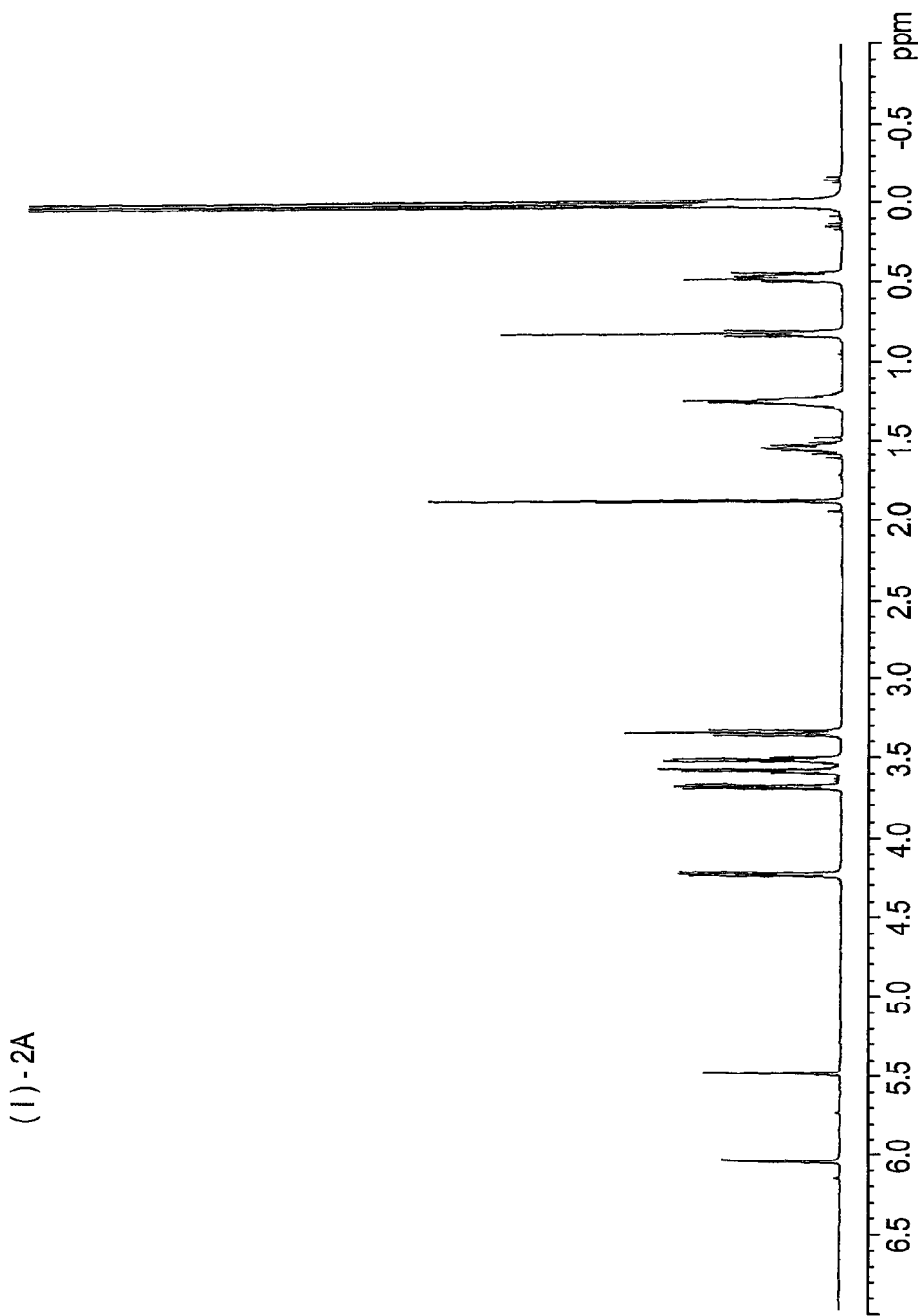
FIG. 2 shows $^1$H-NMR spectra of the silicone which was prepared in Example 2.

In the following formula (1),

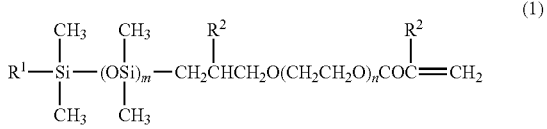

m is an integer of from 3 to 10, preferably of from 4 to 7, and most preferably 4. If m is less than the afore-mentioned lower limit, the oxygen transmission ratio is low. If m exceeds the afore-mentioned upper limit, the hydrophilicity is low. n is an integer of from 1 to 10, preferably from 1 to 4, and most preferably 1 or 2. If n is 0, the compatibility with a hydrophilic monomer is bad. If n exceeds the afore-mentioned upper limit, the strength of the resulting copolymer is low. $R^1$ is an alkyl group having 1 to 4 carbon atoms, preferably a butyl group, and $R^2$ is a hydrogen atom or a methyl group.

The silicone compound of the present invention is one of the silicone compounds represented by formula (1), i.e., the compound which has a specific one value for m, n, $R^1$ and $R^2$, and a purity of 95% by weight or higher, preferably 99% by weight or higher. The purity is determined in gas chromatography, hereinafter referred to as "GC", in the present invention. The details of GC will be described below. If the purity is less than 95% by weight, for instance, a silicone compound which has a different value for m is present in a content of 5% by weight or higher, turbidity occurs sometimes upon mixed with a non-silicone monomer such as 2-hydroxyethyl methacrylate, so that a transparent polymer is not obtained.

Where $R^1$ is a butyl group, m is 4, and n is 1 in the silicone of formula (1), the molecular weight is 412 and the Si moiety accounts for about 70% by weight; and where n is 2, the Si moiety accounts for about 66% by weight. With a silicone compound having such a large Si moiety, a resulting copolymer has high oxygen transmission.

The present invention also provides a process suitable for preparing the afore-mentioned silicone compound. The process is characterized in that the process comprises a step wherein the silicone compound represented by the following formula (2)

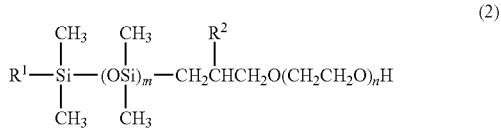

(2)

wherein m, n, $R^1$ and $R^2$ are as defined above, is reacted with a (meth)acrylic acid halide represented by the following formula (3)

(3)

wherein X is Cl, Br, or I and $R^2$ is as defined above. The reaction is preferably carried out in such a manner that the acid halide of formula (3), preferably acid chloride, is slowly added to a solution of the polyorganosiloxane of formula (2) in toluene or hexane at a temperature of from 0 to 50 degrees C with cooling, for instance, in a water bath.

The afore-mentioned reaction is carried out preferably in the presence of an acid trapping agent, so that a higher yield is attained. As the acid trapping agent, use is made of various amines, such as for instance, triethylamine and pyridine, preferably triethylamine. The amount of the acid trapping agent is about 1 to 2 moles per mole of the acid halide of formula (2).

(Meth)acrylic acid halide with high purity is preferred because the purity of the acid halide affects the purity of the resulting silicone compound (1). (Meth)acrylic acid chloride with a purity of 99% or higher is commercially available. This is preferably used and almost no side reaction occurs.

The unreacted silicone compound (2) is monitored in GC. After disappearance of its peak is confirmed, water is poured into the reaction mixture, which is stirred and, then, allowed to stand still to separate into an organic phase and a water phase. The organic phase is washed several times with water and, then, the solvent in the organic phase is stripped to obtain a desired product with a GC purity higher than 95% by weight. The purity is based on a ratio of peak areas in GC. When FID is used, a peak area is proportional to the number of carbon atoms and, therefore, is almost equal to percentage by weight in the product.

The silicone compound of the afore-mentioned formula (2) can be prepared by addition reacting a polyorganohydrogen siloxane represented by the following formula (4),

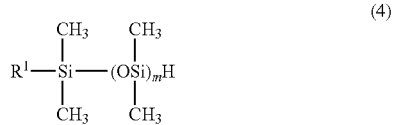

(4)

wherein m and $R^1$ are as defined above,
with a (poly)ethylene glycol mono(meth)allyl ether represented by the following formula (5)

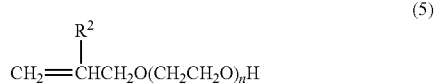

(5)

wherein n is as defined above. The addition reaction is carried out in the presence of a catalyst for addition reaction, such as a compound of platinum family according to a conventional method, where a solvent may be used, such as aliphatic or aromatic solvents such as hexane and toluene; and alcoholic solvents such as ethanol and IPA. 1.2 Moles or more, preferably 1.5 moles or more of the (poly)ethylene glycol mono(meth)allyl ether are used relative to 1 mole of the polyorganohydrogen siloxane. As the (poly)ethylene glycol mono(meth)allyl ether, use is made of, for instance, ethylene glycol monoallyl ether and diethylene glycol monoallyl ether. The reactants may be reacted all together. Preferably, the (poly)ethylene glycol mono(meth)ally ether is placed into a reactor, optionally diluted with a solvent, and a hydrosilylation catalyst of platinum family is added, to which the polyorganohydrogen siloxane is added dropwise at room temperature or a higher temperature to react. After the completion of the addition, the reaction mixture is aged under heating, until disappearance of the peak of the raw material, polyorganohydrogen siloxane, is confirmed, for instance, in GC. Thus, the termination of the reaction can be confirmed. Therefore, there is not a problem that the polyorganohydrogen siloxane remains.

After the completion of the addition reaction, in order to remove excessive (poly)ethylene glycol mono(meth)allyl ether from the reaction liquid, the reaction liquid is subjected to stripping under reduced pressure, or washed with ion exchanged water or an aqueous sodium sulfate solution to extract the (poly)ethylene glycol mono(meth)allyl ether into an aqueous phase. There, a proper amount of solvent, such as toluene and hexane, may preferably be used to better separate the two phases. The solvent is stripped from the organic phase under reduced pressure, whereby the silicone compound of the aforementioned formula (2) is obtained with such a high purity as 97% or higher. The silicone compound may be distilled twice or more to further increase the purity.

The polyorganohydrogen siloxane of the afore-mentioned formula (4) can be prepared by a known method. For instance, the compound of formula (4) wherein $R^1$ is a butyl group and m=4 can be prepared by first preparing $BuMe_2SiOLi$ using BuLi, subjecting hexamethyltrisiloxane to a ring-opening reaction using the $BuMe_2SiOLi$ as an initiator, and terminating the reaction with dimethylchlorosilane. The product is purified by distillation to obtain the product with a purity of 99% or higher. For instance, monobutyl decamethyl hydropentasiloxane represented by formula (4), wherein $R^1$ is a butyl group and m=4, has a boiling point of 110 degrees C/2 mmHg. This may be subjected to addition reaction with (poly)ethylene glycol mono(meth)allyl ether of formula (5) and then to distillation. However, the product of the addition reaction has a higher boiling point. Therefore, the monobutyl decamethyl hydropentasiloxane is preferably distilled to increase its purity before the addition reaction, so that the silicone compound of the afore-mentioned formula (2) may be obtained with a high purity.

The silicone compound of formula (2) may also be obtained by converting a hydroxyl group in the (poly)ethylene glycol (meth)allyl ether to a silyl ester with a sililating agent such as hexamethyldisilazane, carrying out the aforementioned addition reaction, and hydrolyzing the silyl ester.

The silicone compound of the present invention is copolymerized with another monomer to form a polymer. Examples of another monomer include acrylic monomers, such as (meth)acrylic acid, methyl(meth)acrylate, ethyl(meth)acrylate, polyalkylene glycol mono(meth)acrylate, polyalkylene glycol monoalkyl ether(meth)acrylate, trifluoroethyl(meth)acrylate, 2-hydroxyethyl(meth)acrylate, and 2,3-dihydroxypropyl(meth)acrylate; acrylic acid derivatives, such as N,N-dimethyl acrylamide, N,N-diethyl acrylamide, N-acryloyl morpholine, and N-methyl(meth)acrylamide; the other ethylenically unsaturated aliphatic or aromatic acids, such as crotonic acid, cinnamic acid, and vinyl benzoic acid; and polymerizable group-containing silicone compounds.

EXAMPLES

The present inventions will be explained more specifically with reference to the following Examples. However, the present invention shall not be limited thereto.

Example 1

(i) Preparation of a Silicone Compound of the Following Formula (2*)

To a one-litter flask equipped with a Dimroth, a thermometer, and a dropping funnel were added 76.5 g (0.75 mol) of ethylene glycol monoallyl ether and 100 g of toluene and heated to 70 degrees C. To the flask was added 0.38 g of a solution of a catalyst, complex of alkali-neutralized chloroplatinic acid with vinyl siloxane, in toluene (platinum content: 0.5%). Then, 206 g (0.5 mol) of 1-butyl-9-hydro-1,1,3,3,5,5,7,7,9,9-decamethylpentasiloxane was added dropwise to the flask using the dropping funnel over one hour. The inner temperature rose up to 85 degrees C. The reaction mixture was aged at 100 degrees C. for one hour and, then, analyzed in GC. The peak of the raw material, monobutyl decamethyl hydropentasiloxane, disappeared, showing that the reaction completed. 200 g of ion exchanged water of was added to the reaction mixture. The reaction mixture was washed with with stirring, and allowed to stand still for phase separation. The aqueous phase containing excessive ethyleneglycol monoallyl ether was removed. Similarly, the organic phase was washed twice with 200 g of ion exchanged water and the toluene in the organic phase was stripped off under reduced pressure to obtain 242 g of the silicone compound of the following formula (2*) in a yield of 94%. The purity of the silicone compound was 99.4% by weight as determined in GC in the following conditions.

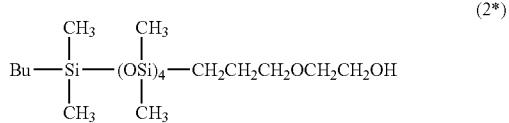

Measuring Method of the Purity of a Silicone Compound (GC Method)
Gas chromatograph: produced by Agilent Technologies
Detector:FID, temperature of 300 degrees C.
Capillary column: HP-5MS (0.25 mm×30 m×0.25 micrometer) from J & W
Temperature rise program: 50 degrees C. for 5 minutes, 10 degrees C./minute, and maintained at 250 degrees C.
Temperature at an injection point: 250 degrees C.
Carrier gas: helium (1.0 ml/minute)
Split ratio: 50:1
Injection volume: 1 microlitter (ii) Preparation of a Silicone Compound of the Following Formula (1*)-1A To a two-liter flask equipped with a Dimroth, a thermometer, and a dropping funnel were added 205.6 g (0.4 mol) of the resulting silicone compound of formula (2*), 50.6 g (0.5 mol) of triethylamine as a de-hydrochloric acid agent, and 500 g of hexane. Then, a mixture of 48.1 g (0.46 mol) of methacrylic acid chloride with 50 g of hexane was added over one hour while cooling the flask in a water bath. The inner temperature rose from 20 degrees C. up to 30 degrees C. The water bath was removed and the reaction mixture was aged at room temperature while monitoring the peak of the silicone compound of formula (2*) in GC. 10 Hours later, the intensity of the peak of the silicone compound of formula (2*) fell down below the detection limit and, then, 500 g of ion exchanged water was added to the reaction liquid to wash. The reaction liquid was allowed to stand still to separate. The aqueous phase was removed. The organic phase was washed further twice with water. The solvents, hexane and so on, were stripped off from the organic phase under reduced pressure to obtain 206 g of a colorless transparent liquid, silicone compound of formula (1*)-1A, in a yield of 89%. The purity of the silicone compound was 98.5% as determined by GC. $^1$H-NMR analysis (300 MHz) showed that the obtained compound was the desired methacrylic silicone. When the silicone compound of formula (1*)-1A was mixed with the same amount of 2-hydroxyethyl methacrylate (HEMA), they dissolved each other to give a transparent solution. They were copolymerized to give a copolymer in a yield of almost 100%. The strength of the resulting copolymer was good.

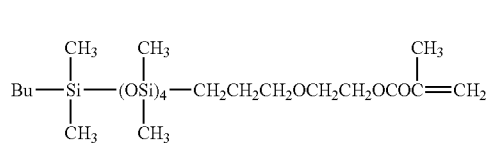

Example 2

(i) Preparation of a Silicone Compound of Formula (4*)

Reaction was carried out as in the case of (2*) except that 109.5 g (0.75 mol) of diethylene glycol monoallyl ether was used instead of 76.5 g of ethylene glycol monoallyl ether of formula (2*). After the completion of the reaction, the reaction mixture was washed with 200 g of ion exchanged water. The separation was not enough and, therefore, water was changed with an aqueous 5% sodium sulfate solution. The toluene in the aqueous phase was stripped off under reduced pressure to obtain 240 g of the silicone compound of the following formula (4*) in a yield of 87%. The purity of the compound was 99.1% by weight as determined on GC in the afore-mentioned conditions.

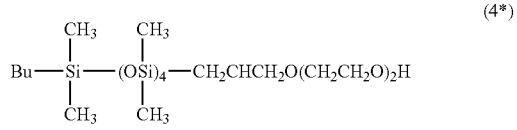

(ii) Preparation of a Silicone of (1*)-2A

Reaction was carried out as in the case of synthesis of (1*)-1A, except that 223.2 g (0.4 mol) of the silicone carbinol (4*) was used instead of 205.6 g of the silicone carbinol (2*). An aqueous 5% sodium sulfate solution was used instead of ion exchanged water in washing. In the final stage, the solvent, hexane and so on, were stripped off under reduced pressure to obtain 213 g of a colorless transparent liquid, silicone compound of the following formula (1*)-2A, in a yield of 85%. The purity of the silicone compound was 97.7% by weight, as determined in GC. $^1$H-NMR analysis showed that it was the desired methacrylic silicone. When (1*)-2A was mixed with the same amount of HEMA, they dissolve each other to give a transparent solution. They were copolymerized to give a copolymer in a yield of almost 100%. The strength of the resulting copolymer was good.

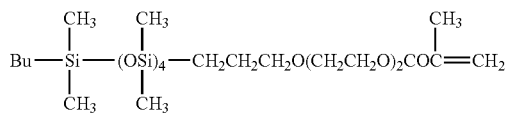

(1*)-2A

Comparative Example 1

Reaction was carried out according to the method described in Patent Literature 3. That is, a solution of BuMe$_2$SiOLi (1 mol) in THF was cooled to 0 degree C. and a solution of 1 mol of hexamethyltrisiloxane in THF was added. The reaction was carried out at 0 degree C. 3 Hours later, the amount of the hexamethyltrisiloxane became 5% or less of the initial amount and, then, 3-(2-methacryloyloxyethoxy)propyl dimethylchlorosilane was added to terminate the reaction. The reaction mixture was worked up and then THF was stripped off from the reaction mixture. The end-blocking ratio was 95%, as calculated from the acryl equivalent. The product contained about 70% of the desired pentameric silicone, about 5% of the dimeric silicone, and about 25% of the octameric silicone.

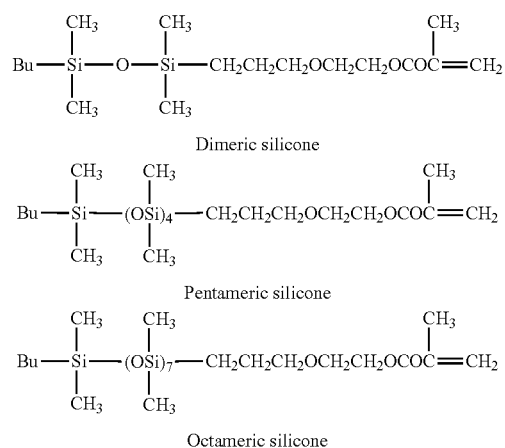

This caused white turbidity when mixed with the same amount of HEMA and, therefore, cannot be used as a monomer for obtaining a transparent copolymer.

Comparative Example 2

The reaction was terminated with dimethylchlorosilane instead of 3-(2-methacryloyloxyethoxy)propyldimethylchlorosilane used in Comparative Example 1 THF was stripped off under reduced pressure to obtain a siloxane having a hydrogen on one end with a ratio of pentameric silicone/octameric silicone=70/25. 1.5 Moles of PKA-5001 (from Nippon Oil & Fats Corporation; average molecular weight: 200, repeating units of ethyleneoxide: 3.2) was reacted with 1 mole of this SiH silicone in toluene according to the method described in Patent Literature 4. Excessive PKA-5001 was extracted with methanol and, then, toluene was stripped off from the reaction liquid to obtain a polyether siloxane having a terminal hydroxyl group. This hydroxyl group was esterified with dicyclohexylcarbodiimido, dimethylaminopyridine, and methacrylic acid. The reaction liquid was worked up to obtain a colorless transparent liquid. The end-blocking ratio was 95%, as calculated from acryl equivalent. When this mixture of pentameric silicone/octameric silicone was mixed with the same amount of HEMA, a colorless transparent solution was formed. They were copolymerized, and the content of the silicone which did not copolymerize was 6% by weight. The strength of the copolymer was low because the copolymer contained the octameric silicone which has a high molecular weight. Thus, it was found that the silicone cannot be used as a copolymerizable monomer for ophthalmic lenses, particularly contact lenses.

INDUSTRIAL APPLICABILITY

The present silicone compound has a high purity and is preferably used for preparing an ophthalmic device. The present process is suitable for preparing the silicone compound with a high purity.

The invention claimed is:

1. A process for preparing a silicone compound represented by the following formula (1),

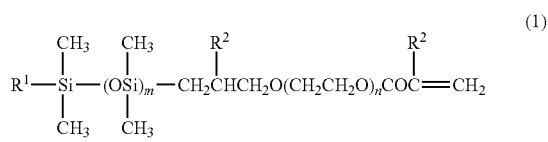

wherein m is one value out of an integers of from 4 to 10, n is one value out of 1 and 2, $R^1$ is an alkyl group having 1 to 4 carbon atoms, and $R^2$ is a hydrogen atom or a methyl group, characterized in that the process comprises steps of:

(i) reacting a polyorganohydrogen siloxane represented by the following formula (4),

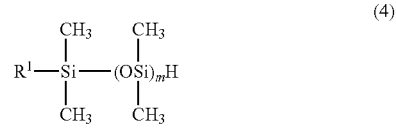

wherein $R^1$ and m are as defined above
with a (poly)ethylene glycol mono(meth)allyl ether represented by the following formula (5),

wherein n is as defined above, to prepare a silicone compound represented by the following formula (2),

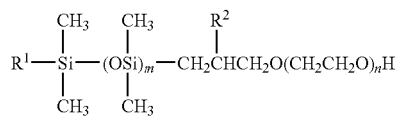

wherein m, n, $R^1$ and $R^2$ are as defined above, and (ii) reacting the silicone compound represented by the formula (2) with a (meth)acrylic acid halide represented by the following formula (3),

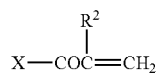

wherein X is Cl, Br, or I and $R^2$ is as defined above, and wherein the silicone compound comprises one silicone compound having a specific one value for m with a purity of 95% by weight or higher.

2. The process according to claim 1, characterized in that said reaction is carried out in the presence of an acid trapping agent.

3. The process according to claim 2, wherein the acid trapping agent is triethylamine.

4. The process according to claim 1, wherein m in formula (1) is 4.

5. The process according to any one of claims 1 to 3 and 4, wherein $R^1$ in formula (1) is butyl.

6. A process for the preparation of an ophthalmic device, comprising steps of:

(a) preparing a silicone compound represented by the following formula (1),

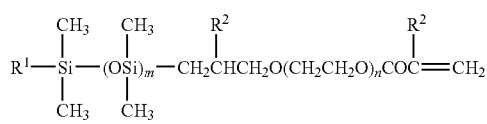

wherein m is one value out of integers of from 4 to 10, n is one value out of 1 and 2, $R^1$ is an alkyl group having 1 to 4 carbon atoms, and $R^2$ is a hydrogen atom or a methyl group; characterized in that the process comprises steps of:

(i) reacting a polyorganohydrogen siloxane represented by the following formula (4),

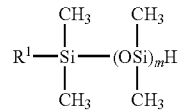

wherein $R^1$ and m are as defined above with a (poly) ethylene glycol mono(meth)allyl ether represented by the following formula (5),

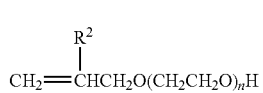

wherein n is as defined above, to prepare a silicone compound represented by the following formula (2),

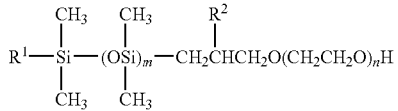

wherein m, n, $R^1$ and $R^2$ are as defined above, and (ii) reacting the silicone compound represented by the formula (2) with a (meth)acrylic acid halide represented by the following formula (3),

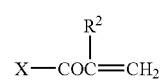

wherein X is Cl, Br, or I and $R^2$ is as defined above; and wherein the silicone compound comprises one silicone compound having a specific one value for m with a purity of 95% by weight or higher, and (b) copolymerizing the silicone compound represented by the formula (1) prepared in the step (a) with at least one ethylenically unsaturated monomer selected from the group consisting of acrylic monomers, acrylic acid derivatives, other ethylenically unsaturated aliphatic or aromatic acids, and polymerizable group-containing silicone compounds.

7. The process according to claim 6, wherein the acrylic monomer is selected from the group consisting of (meth) acrylic acid, methyl (meth)acrylate, ethyl (meth)acrylate, polyalkylene glycol mono(meth)acrylate, polyalkylene glycol monoalkyl ether (meth)acrylate, trifluoroethyl (meth)acrylate, 2-hydroxyethyl (meth)acrylate, and 2,3-dihydroxypropyl (meth)acrylate; the acrylic acid derivative is selected from the group consisting of N, N-dimethyl acrylamide, N, N-diethyl acryl amide, N-acryloyl morpholine, and N-methyl (meth)acrylamide; and the other ethylenically unsaturated aliphatic or aromatic acid is selected from the group consisting of crotonic acid, cinnamic acid and vinyl benzoic acid.

8. The process according to claim 6, wherein m in formula (1) is 4.

9. The process according to claim 6, wherein $R^1$ in formula (1) is butyl.

* * * * *